United States Patent [19]
Chang

[11] Patent Number: 5,474,780
[45] Date of Patent: * Dec. 12, 1995

[54] MONOLITHIC MALEIC ANHYDRIDE DRUG DELIVERY SYSTEMS

[75] Inventor: James N. Chang, Irvine, Calif.

[73] Assignee: Allergan, Inc., Irvine, Calif.

[*] Notice: The portion of the term of this patent subsequent to Dec. 22, 2009, has been disclaimed.

[21] Appl. No.: 30,479

[22] PCT Filed: Apr. 19, 1991

[86] PCT No.: PCT/US91/02712

§ 371 Date: Mar. 30, 1993

§ 102(e) Date: Mar. 30, 1993

[87] PCT Pub. No.: WO91/16869

PCT Pub. Date: Nov. 14, 1991

Related U.S. Application Data

[63] Continuation-in-part of Ser. No. 516,110, Apr. 27, 1990, abandoned.

[51] Int. Cl.⁶ .............................. A61K 9/16; A61K 9/22; A61K 9/24; A61K 9/52
[52] U.S. Cl. .......................... 424/428; 424/426; 424/486; 424/501; 424/443; 526/936
[58] Field of Search ..................................... 424/486, 426, 424/428, 501; 526/936, 318.2, 318.25

[56] References Cited

U.S. PATENT DOCUMENTS 3,993,071 11/1976 Higuchi et al. ........................ 128/260
4,249,531 2/1981 Heller et al. ............................ 128/260
4,304,765 12/1981 Shell et al. ................................. 424/14
4,407,792 10/1983 Schoenwald et al. .................... 424/81
4,615,697 10/1986 Robinson ................................. 604/890
5,173,298 12/1992 Meadows ................................. 424/426

FOREIGN PATENT DOCUMENTS 8910740 11/1989 WIPO .

OTHER PUBLICATIONS

Mortada, Sana A. M., et al., "Preparation of microcapsules from complex coacervation of Gantrez-gelatin. II. In vitro dissolution of nitrofurantoin microcapsules," J. Microencapsulation, 1987, vol. 4, No. 1, pp. 23-37.

Schoenwald, R. D., et al., "Influence of High-Viscosity Vehicles on Miotic Effect of Pilocarpine," J. of Pharm. Sciences, vol. 67, No. 9, Sep. 1978, pp. 1280-1283.

Mortada, Sana A., "Preparation of Microcapsules Using the n-Butyl Half-Ester of PVM/MA Coacervate System," Pharmazie, vol. 36, No. 6, 1981, pp. 420-423.

Primary Examiner—Edward J. Webman
Attorney, Agent, or Firm—Poms, Smith, Lande & Rose

[57] ABSTRACT

Erodible bioadhesive drug delivery vehicles for use in delivering pharmaceutical compounds to the eye and similar physiological environments are disclosed. The drug delivery vehicles are formed of a homopolymer or copolymer of maleic anhydride or lower alkyl maleic anhydride incorporating a pharmaceutical compound in either a monolithic matrix or encapsulated form. The bioadhesive erodible drug delivery vehicles are configured to be retained in the eye following administration while providing specific erosion profiles allowing convenient drug delivery schedules ranging from hourly to daily or weekly intervals.

36 Claims, 2 Drawing Sheets

MONOLITHIC MALEIC ANHYDRIDE DRUG DELIVERY SYSTEMS

REFERENCE TO EARLIER APPLICATION

This application is a continuation-in-part of application Ser. No. 07/516,110, filed Apr. 27, 1990, now abandoned.

FIELD OF THE INVENTION

The present invention relates in general to an erodible, sustained release polymeric drug delivery vehicle. More particularly, the present invention is directed to drug delivery systems including a homopolymer or copolymer of maleic anhydride or lower alkyl maleic anhydride intended for use in treating ocular conditions and in similar physiologic environments. The erodible polymer system simplifies the application and removal of the drug delivery system and may be configured to provide specific erosion profiles allowing drug delivery administration to be scheduled at convenient daily or weekly time intervals.

BACKGROUND OF THE INVENTION

A problem with the administration of many pharmaceutical medicaments and diagnostic compounds has been the need to retain sufficient quantities of these compounds in contact with the target tissues and systems for a sufficient period of time to accomplish the therapeutic or diagnostic purpose. This problem is particularly acute in connection with compounds administered to the eye. In the ocular environment, tear turnover and drainage through the lacrimal system quickly remove a major portion of any compound administered to the eye so that only a small fraction of the original dosage remains in the eye for an extended period of time. As a result, the repeated administration of relatively large dosages is required to compensate for this loss and to ensure that an effective concentration of the desired pharmaceutical agent remains in contact with the eye. Similar problems are also encountered in connection with the nasal mucosa, oral cavity and similar physiologic environments.

An alternative approach to ophthalmic drug retention in the eye has been the use of viscous ointments and gels designed to slow down the rapid loss of pharmaceutical compounds. These semi-solid drug containing compounds are applied directly to the conjunctiva of the eye and remain in the cul de sac until physically or mechanically removed. Though reasonably effective at retaining adequate drug dosages in contact with the surface of the eye, a major disadvantage associated with ointments and gels is the difficulty of delivering a controlled dosage with such widely variable systems. To date, it has not been possible to deliver preformed gels from multiple dose containers in a ready and convenient fashion. Moreover, previously known drug containing ointments and gels may form barriers to sight as well as forming aesthetically unpleasant crusting along the edges of the eyelids. This and possible blockage of the lacrimal duct may lead to decreased patient acceptability and utilization of such systems.

Another approach to the solution of these problems has been the utilization of drug containing ocular inserts. Typically, these devices are formed of microporous solid polymers incorporating a reservoir of the drug or diagnostic agent required. Shaped as a small disc, barrel or strip, these devices are inserted into the cul de sac of the eye where they remain for periods of several days or weeks while the pharmaceutical compounds contained therein continuously diffuse into the lacrimal fluids. A significant disadvantage associated with such solid insert devices is that many patients, especially the elderly, have a difficult time inserting or removing a solid object from the cul de sac of the eye. As a result, it is often necessary for medical personnel to position such devices as well as to remove them at the end of their useful life. What is more, currently available ocular inserts often fall out of position from the eye. Additionally, these devices may be uncomfortable when placed in the eye.

Another alternative approach to the solution of these problems has been the utilization of drug delivery compounds which are liquid at room temperature, but which form semi-solid compounds when warmed to body temperatures. Similarly, compositions which transform from liquids to semi-solids in response to changes in pH have also been proposed. Though effective at their intended purposes, such compounds may suffer from many of the drawbacks associated with ointments and gels and still may require repeated administration throughout the day.

Alternatively, bioerodible microparticulate suspensions have also been utilized for the delivery of ophthalmic drugs. For example, U.S. Pat. No. 4,001,388 discloses an orthoester homopolymer drug containing microparticulate suspended in a liquid carrier such as physiological saline, silicone oil, mineral oil and the like. Similarly, U.S. Pat. No. 4,865,846 discloses a drug delivery system formed of a liquid and ointment carrier containing an ophthalmic drug and a bioerodible particulate carrier incorporating additional drugs. The bioerodible feature is designed to prevent the buildup of particulate material in the eye, as well as to provide controlled drug release. However, in practice, significant loss through the lacrimal drainage system decreases the effectiveness of such delivery systems.

Accordingly, it is a principal object of the present invention to provide a sustained release drug delivery vehicle for use in treating or diagnosing ophthalmic conditions as well as for use in physiological environments similar to the ocular milieu.

It is an additional object of the present invention to provide an erodible ocular drug delivery vehicle which can be installed in the cul de sac of the eye without need for professional medical assistance and which obviates the need for subsequent removal of the vehicle by the patient or medical personnel.

It is a further object of the present invention to provide an ophthalmic drug delivery vehicle which is self-lubricating for patient comfort, yet which exhibits muco-adhesive properties for retention on the conjunctival mucosa.

It is a further additional object of the present invention to provide an ophthalmic drug delivery vehicle that can be conveniently administered in controlled dosages at daily or weekly intervals, or more often if desired.

SUMMARY OF THE INVENTION

Generally stated, the present invention accomplishes the above-described objectives by providing polymeric drug delivery vehicles which exhibit self-adhesive and bio-adhesive properties, yet which slowly erode in a controlled fashion to provide the sustained release of pharmaceutical or diagnostic compounds while eliminating the need for medical assistance to install or remove the drug delivery system. What is more, the polymeric drug delivery vehicles of the present invention may be configured to comfortably remain in contact with the surface of a patient's eye for periods of hours, days, or even up to one week or more.

More particularly, the polymeric drug delivery vehicles of the present invention utilize an encapsulating membrane or supporting monolithic matrix formed of a homopolymer or copolymer of maleic anhydride or lower alkyl maleic anhydride which is designed to hydrolyze and erode in a controlled manner in order to slowly remove the drug delivery vehicle from the target site through the normal turnover of physiological fluids such as is encountered with tear turnover and lacrimal drainage in the eye. As those skilled in the art will appreciate, the erosion of the polymeric drug delivery vehicle also facilitates the release of encapsulated pharmaceutical agents or diagnostic compounds which may be coated by the polymer or homogeneously incorporated into the polymer matrix. Moreover, polymer erosion also serves to coat the surface of the drug delivery vehicle with a self-lubricating layer of hydrolyzed polymer. Though it would normally be expected that such self-lubricating action would make placement of the drug delivery vehicle unstable, the unique polymeric drug delivery vehicle of the present invention exhibits mucoadhesive properties which facilitate its retention at the target site throughout the controlled erosion process.

In accordance with the teachings of the present invention, the polymeric drug delivery vehicles of the present invention can be formed into a variety of three-dimensional structures and configurations ranging from microparticulates to microcapsules to ocular inserts. In this manner, the available surface area and hence the rate of erosion can be controlled to produce drug delivery vehicles which will remain on site for specific periods of time. Preferably, the microparticulate or microcapsule configuration will be sized to provide a 12 to 24 hour erosion profile for convenient, once a day administration, though shorter profiles are also contemplated as being within the scope of the present invention. For longer treatment periods, the drug delivery vehicles of the present invention can be formed as macroscopic inserts which will remain in place for periods on the order of one week. However, in direct contrast to the prior art gels and insert devices which may require skilled medical personnel to remove the devices, the drug delivery vehicles of the present invention will slowly erode over the intended time period to the point where the drug delivery vehicle has been completely removed from the target site at the end of its anticipated useful life.

It is contemplated as being within the scope of the present invention to suspend the microparticulate or microcapsule form of the polymeric drug delivery vehicles in an aqueous or non-aqueous solution for drop installation where desired. As those skilled in the art will appreciate, aqueous suspensions will require formulation immediately prior to administration whereas non-aqueous solutions can be formulated and stored over considerably longer periods of time prior to administration. Additionally, it should also be noted that the adhesive properties of the homopolymer or copolymer of maleic anhydride or lower alkyl maleic anhydride cause the microparticulate or microcapsule forms of the drug delivery vehicles to self-adhere following hydrolyzation to form a unified agglomeration which remains in place following administration.

As will be discussed in detail below, a wide variety of therapeutic and diagnostic agents may be utilized with the polymeric drug delivery vehicle of the present invention. These compounds can be incorporated into an homogeneous monolithic matrix to form microparticulates or macroscopic ocular inserts. Alternatively, the pharmaceutical agents can be encapsulated by a layer or membrane of the polymer as desired. Each configuration provides alternative drug release and erosion profiles which can be modified or combined to produce optimal therapeutic benefit.

Further objects and advantages of the polymeric drug delivery vehicles of the present invention, as well as a better understanding thereof, will be afforded to those skilled in the art from a consideration of the following detailed explanation of preferred exemplary embodiments thereof. Reference will be made to the appended sheets of drawings which will now be first described briefly.

DETAILED DESCRIPTION OF PREFERRED EMBODIMENTS

Figure 1:
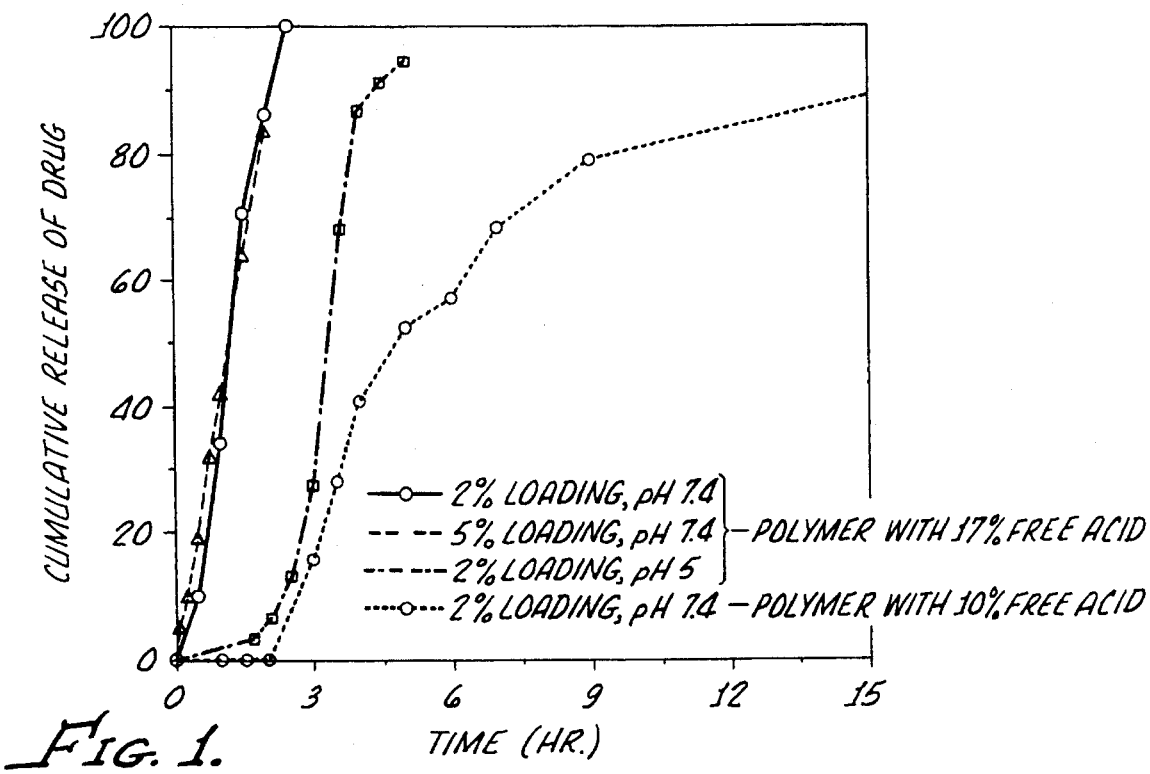
FIG. 1 is a graphical illustration showing the release of various concentrations of dipivefrin (DPE) over time from poly(methylvinylether/maleic anhydride) copolymers containing different amounts of free acid illustrating the principles of the present invention.

In a broad aspect, the drug delivery vehicles of the present invention comprise a homopolymer or copolymer of maleic anhydride or lower alkyl maleic anhydride incorporating a therapeutic or diagnostic pharmaceutical compound. Because of the unique controlled hydrolysis and erosion properties exhibited by these compounds, the drug delivery vehicles formed in accordance with the teachings of the present invention are particularly well suited for use in connection with the diagnosis or treatment of injuries or diseases of the eye. However, those skilled in the art will appreciate that the drug delivery vehicles of the present invention are also well suited for use in biological systems exhibiting physiologic fluid turnover analogous to that of the lacrimal secretions common to the surface of the eye. Accordingly, for purposes of explanation and without limiting the scope of the present invention, the following exemplary embodiments will be discussed in the context of ocular drug delivery systems intended for use in delivering ophthalmic compounds. However, these teachings are readily applicable to alternative physiologic systems.

More particularly, an exemplary ocular drug delivery vehicle produced in accordance with the teachings of the present invention can be formed from a homopolymer of maleic anhydride or lower alkyl maleic anhydride or a copolymer of maleic anhydride or lower alkyl maleic anhydride and another comonomer incorporating from approximately 1% by weight to 60% by weight therapeutic or diagnostic pharmaceutical compound. The pharmaceutical compound of choice can be incorporated within the polymer to form a monolithic matrix or, alternatively, can be encapsulated by the polymer to form a microcapsule. Each alternative configuration has its own attendant advantages and features.

For example, the monolithic matrix form of the copolymer drug delivery vehicle can be produced as a plurality of microparticulates preferably sized on the order of approximately 2 μm to 200 μm. This configuration provides the highest degree of surface area and therefore the associated factors of drug delivery rate and erosion rate are highest. Alternatively, the monolithic matrix drug delivery vehicle can be formed as an insert sized on the order of 500 μm to 5,000 μm. At this macroscopic size, the surface area to volume ratio of the monolithic matrix is significantly reduced and, as a result, the drug release profile and erosion profile is also concomitantly reduced.

As an additional alternative, the drug delivery vehicle can be formulated in the microcapsule configuration wherein each microcapsule is preferably sized to be on the order of 2 μm to 200 μm. While the surface area to volume ratio in this latter configuration is analogous to that produced with the microparticulate monolithic matrix form of the drug delivery vehicle, the drug loading can be considerably higher. Thus, it is contemplated as being within the scope of the present invention to form microparticulates and solid inserts from a monolithic matrix of a homopolymer of maleic anhydride or lower alkyl maleic anhydride or a copolymer of maleic anhydride or lower alkyl maleic anhydride and another comonomer incorporating from approximately 1% to 20% by weight pharmaceutical compound. Alternatively, it is also contemplated as being within the scope of the present invention to produce microcapsules of such homopolymers or copolymers incorporating from approximately 2% to 60% by weight pharmaceutical compound. Each of the foregoing alternative embodiments of the drug delivery vehicle of the present invention exhibits a unique controlled hydrolysis and resultant controlled erosion profile that is particularly well suited to utilization in the ocular milieu and other analogous physiological systems.

Preferably, the comonomers and/or the lower alkyl maleic anhydride comprising the polymeric drug delivery systems of the present invention are selected to provide a polymer exhibiting a decreased hydrophilicity relative to maleic anhydride homopolymer. Thus, in accordance with the teachings of the present invention the drug delivery vehicle will preferably include a lower alkyl maleic anhydride or a comonomer suitable for decreasing the hydrophilicity of the resulting polymer as compared to that of maleic anhydride homopolymer. More particularly, the maleic anhydride or the lower alkyl maleic anhydride containing homopolymers and copolymers of the present invention erode through hydrolysis to carboxylic radicals (for example, carboxylic acid and carboxylate radicals). In maleic anhydride homopolymer, the ratio of carbon atoms to carboxylic radicals is 2. Copolymerization of maleic anhydride with comonomers to increase the ratio of carbon atoms to carboxylic radicals from 2 to a preferable range of from about 3 to about 7 and, most preferably to about 3.5, functions to decrease the hydrophilicity of the copolymer and, as a result, retards the rate of hydrolysis and the associated release rate of the incorporated pharmaceutical compound. Similarly, replacing all or a portion of the maleic anhydride with a lower alkyl maleic anhydride will increase the ratio of carbon atoms to carboxylic radicals and thus retard the rate of hydrolysis.

As those skilled in the art will appreciate, to achieve the desired decrease in hydrophilicity the comonomer constituent should be substantially free of hydrophilic groups. Accordingly, hydrocarbon comonomers and hydrocarbon comonomers substituted with non-hydrophilic substituents are preferred. Exemplary non-hydrophilic substituents which may be substituted on the comonomers of the present invention include: —X, —O—R,

wherein X is a halogen radical (for example, a fluorine or chlorine radical) and R is an alkyl radical, (for example, a $C_{1-12}$ and preferably, a $C_{1-8}$ alkyl radical).

Thus, the following exemplary comonomers may be copolymerized with maleic anhydride to produce maleic anhydride copolymers within the scope and teachings of the present invention: $C_{1-4}$ lower alkyl vinylethers including methylvinylether, butadiene, styrene, isoprene, ethylene, propylene, vinylchloride, and $C_{1-8}$ alkylesters of acrylic acid or methacrylic acid, including n-butylacrylate, 2-ethylhexylacrylate, methylmethacrylate, vinyl acetate, vinyl crotonate, vinylidene chloride, and the like. Preferably, the comonomer will be a lower alkyl vinylether such as methylvinylether.

In accordance with the teachings of the present invention the ratio of comonomer to maleic anhydride will vary from 0 to approximately 3 and preferably from about 1 to 2. Most preferably the comonomer to maleic anhydride or lower alkyl maleic anhydride ratio is about 1 and the copolymer is poly(methylvinylether/maleic anhydride), a hydrophobic polymer of the following general structure:

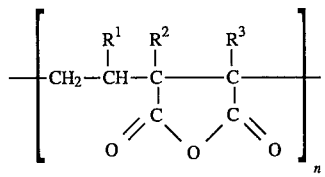

Wherein $R^1$ is $OCH_3$ and $R^2$ and $R^3$ are each hydrogen. Available from GAF under the trade name Gantrez AN®, poly(methylvinylether/maleic anhydride) can be purchased in a variety of number-averaged molecular weights reported as ranging from 20,000 to 100,000. As those skilled in the art will appreciate, on a weight-averaged basis these same copolymers are reported as having molecular weights ranging from 250,000 to 1,100,000. The copolymer is relatively non-toxic ($LD_{50}$=8 g/kg in white rats) and has a softening point near 225° C. Upon contact with an aqueous medium, the anhydride functionalities of the copolymer readily hydrolyze to form the free acid. This initial hydrolysis leads to the formation of a polymeric soft hydrogel and, as hydrolysis proceeds, the copolymer becomes soluble in the surrounding aqueous medium. These properties are independent of molecular weight and thus any of the readily available molecular weight copolymers are suitable for practicing the present invention.

It should be noted that it is contemplated as being within the scope of the present invention to formulate homopolymers or copolymers of lower alkyl maleic anhydride derived from a lower alkyl maleic anhydride monomer having the general structure:

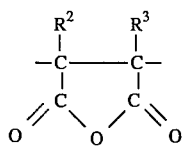

wherein $R^2$ and $R^3$ are selected from the group consisting of hydrogen and lower alkyl ranging from $C_{1-4}$. Preferably, either one of $R^2$ or $R^3$ is hydrogen and the other is lower alkyl. The utilization of these lower alkyl maleic anhydride comonomers alone, or the addition of these lower alkyl substituents to a maleic anhydride copolymer serves to further decrease the hydrophilicity of the maleic anhydride comonomer and the associated erosion rate and drug release profile.

The maleic anhydride or lower alkyl maleic anhydride containing homopolymers or copolymers of the present invention discussed above may be synthesized at moderate temperatures and pressures in the presence of a free radical initiator, or are available commercially. For example, synthesis may be accomplished at temperatures ranging from approximately 40° C. to approximately 80° C. at pressures ranging from approximately 14 psi to approximately 50 psi in the presence of a free radical initiator such as a peroxide. Such homopolymers or copolymers may have a number-averaged molecular weight between 10,000 and 200,000, e.g. between about 50,000 and 100,000.

As will be appreciated by those skilled in the art, once placed in an aqueous environment such as the conjunctival sac of the eye, the drug delivery vehicles of the present invention will rapidly form a soft, self-lubricating gel which slowly dissolves in the tear film and safely erodes from the surface of the eye into the lacrimal drainage system. During this dissolution process, the incorporated drug is continuously released onto the surface of the eye for effective treatment or diagnosis thereof.

Further contributing to the function of the drug delivery system, the bioadhesiveness of the homopolymers or copolymers of maleic anhydride or lower alkyl maleic anhydride of the present invention causes the microparticulates and/or microcapsules to gel together and to adhere to the conjunctiva mucin layer of the eye. This adhesive action ensures retention of the drug delivery system in a non-intrusive way in direct contrast to prior art microparticulates such as polystyrene latex beads (14 μm to 50 μm) which are retained for less than thirty minutes before being expelled from the eye. For example, the mucoadhesive force of poly(methylvinylether/maleic anhydride) is known to be similar to that of polyacrylates such as Carbopol 934® and sodium alginate. This mucoadhesiveness also functions to secure ocular inserts as well.

As illustrated by the following non-limiting examples, the polymeric drug delivery vehicle of the present invention can be formulated utilizing a variety of methods currently known in the art. For example, a monolithic matrix of poly(methylvinylether/maleic anhydride) copolymer incorporating a therapeutic or diagnostic pharmaceutical compound can be formulated by simply dissolving the copolymer and the pharmaceutical agent in a compatible solvent. Removing the solvent through rotary evaporation or vacuum evaporation will produce a film or particulate monolithic matrix loaded with the compound. Particulate size can be adjusted utilizing grinding or milling techniques as known in the art. Alternatively, macroscopically sized monolithic matrix inserts can be cut from the film so produced or formed from the particulates through high pressure molding techniques. Microencapsulation techniques are also known in the art. For example, emulsions can be formed by dissolving the copolymer in an appropriate solvent and adding the pharmaceutical agent of choice which is then coacervated to precipitate the copolymer and encapsulate the pharmaceutical compound therein. Examples of such formation techniques are provided below.

EXAMPLE 1

2.7 g of Gantrez AN-169 copolymer and 0.3 g of DPE●HCl (dipivalyl epinephrine hydrochloride) were dissolved in 100 ml of acetonitrile to form a solution at room temperature in a round bottom flask. Acetonitrile was subsequently removed by evaporation using a rotor-evaporator operated at 40° C. to leave behind a homogeneous, dry monolithic matrix of DPE●HCl and the copolymer. The solid mixture was then ground into microparticles using a Tekmar mill. The resulting microparticles were dried in a vacuum oven for 24 hours to remove any solvent residue. The average particle size of the microparticles was 65 micron. The drug (DPE●HCl) loading in the microparticles was 9.82% w/w as determined by HPLC.

EXAMPLE 2

1.9 g of Gantrez AN-169 copolymer and 0.1 g of levo-bunolol hydrochloride were dissolved in 50 ml of dimethyl formamide to form a solution at room temperature in a round bottom flask. Dimethyl formamide was subsequently removed by evaporation using a rotor-evaporator operated at 70° C. and under high vacuum to leave behind a homogeneous, dry monolithic matrix of levo-bunolol hydrochloride and the copolymer. The solid mixture was ground into microparticles using a Tekmar mill. The resulting microparticles were dried in a vacuum oven for 24 hours to remove any solvent residue. The average particle size of the microparticles was 46 micron. The drug (levo-bunolol hydrochloride) loading in the microparticles was 5.1% w/w as determined by HPLC.

EXAMPLE 3

9.8 g of Gantrez AN-169 copolymer and 0.2 g of 5-bromo- 6-(imidazolin-2-ylamino)-quinoxaline were dissolved in 200 ml of acetone to form a solution at room temperature. A Brinkmann spray dryer was employed to produce small particles from the solution. The particles collected from the spray dryer were agglomerates which were ground to microparticles using a Tekmar mill. The resulting microparticles were dried in a vacuum oven for 24 hours to remove any solvent residue. The average particle size of the microparticles was 41 micron. The drug loading in the microparticles was 2.0% w/w as determined by HPLC.

EXAMPLE 4

1.9 g of Gantrez AN-169 copolymer and 0.1 g of pilocarpine were dissolved in 50 ml of acetonitrile to form a solution at room temperature. The solution was slowly dropped at 50 microliter drop size into mineral oil with stirring. The temperature of the mineral oil was controlled at 50° C. Acetonitrile was evaporated in two hours. The microparticles formed in the mineral oil were spherical in shape with an average size of 50 μm. The microparticles were washed by decantation with petroleum ether to give a free-flowing powder, and were dried in a vacuum oven.

EXAMPLE 5

0.005 g of microparticles prepared from Gantrez AN-169 copolymer containing 5% w/w dipivalyl epinephrine hydrochloride were compression molded into a disk using a Carver laboratory press at room temperature. The disk was 0.5 cm in diameter and 0.03 cm thick.

EXAMPLE 6

0.02 g of microparticles prepared from the Gantrez AN-169 copolymer containing 2% w/w sodium fluorescein were compression molded into a disk using a Carver laboratory press at room temperature. The disk was 0.5 cm in diameter and 0.11 cm thick.

As those skilled in the art will appreciate, the size of the drug delivery vehicle produced in accordance with the teachings of the present invention is partially determinative of the erosion rate and the release rate of the pharmaceutical compound contained therein. Smaller particles will hydrolyze and erode at a more rapid pace than larger particles due to their relatively higher surface area. Microparticulates and microcapsules sized from approximately 5 µm to 50 µm are preferred for drug delivery intervals lasting up to approximately 24 hours. Microparticulates and microcapsules are most readily administered to the target site by suspending the drug delivery vehicles in a liquid carrier such as an aqueous or non-aqueous solution. Those skilled in the art will appreciate that the particle concentration as well as the drug loading can be varied as needed to produce the desired delivery dosage. Exemplary non-aqueous solutions are perfluorhydrocarbons as they eliminate the need to prepare the suspension immediately prior to delivery. However, it is also contemplated as being within the scope of the present invention to utilize aqueous suspensions which are formulated in individual dosages prior to administration.

Conversely, drug delivery inserts may be formed from the monolithic matrix drug delivery vehicle of the present invention for delivery periods of 24 hours or more. Such inserts can be formed through compression molding or cutting from the monolithic matrix films produced in the foregoing examples. Preferably, the inserts will be formed as disks, drums or strips which can be readily inserted into the cul de sac of the eye and comfortably retained in place for periods up to one week or more.

It is also contemplated as being within the scope of the present invention to prepare drug delivery vehicles comprising a mixture of particle sizes or mixtures of microparticles and microcapsules. Such combinations can be designed to provide specific drug release profiles including high initial concentrations or zero order deliveries.

Any pharmaceutical compound which is suitable for therapeutic or diagnostic purposes and is reasonably compatible with homopolymers or copolymers of maleic anhydride or lower alkyl maleic anhydride may be incorporated into the drug delivery vehicle of the present invention. Exemplary pharmaceutical compounds include antibacterials, antihistaminics, anti-inflammatories, miotics and anticholinergics, mydriatics, antiglaucoma compounds, antiparasitic compounds, antivirals, carbonic anhydrase inhibitors, anti-fungal agents, anesthetic agents, peptides, proteins, diagnostic agents and immunosuppressive agents. Preferred pharmaceutical compounds for use in ocular situations include dipivalyl epinephrine hydrochloride (DPE), levo-bunolol hydrochloride, flurbiprofen, 5-bromo-6-(imidazolin-2-ylamino)-quinoxaline, pilocarpine, sodium fluorescein, timolol, betaxolol, ofloxocin, and ibuprofen.

These compounds can be incorporated into the drug delivery vehicle of the present invention in ranges from approximately 2% by weight to approximately 60% by weight. Those skilled in the art will appreciate that the upper level concentration is determined by the form of the ocular drug delivery vehicle as well as the desired delivery period. For example, a monolithic matrix drug delivery vehicle produced in accordance with the teachings of the present invention will contain from approximately 1% by weight to approximately 10% by weight of the pharmaceutical compound. Alternatively, microcapsules may contain from approximately 2% by weight to approximately 60% by weight, with approximately 10% by weight being preferred.

As will be appreciated by those skilled in the art, the polymeric drug delivery vehicles of the present invention may be utilized to deliver pharmaceutical compounds to the eye or other similar physiological systems. This method for delivering pharmaceutical compounds comprises the steps of preparing a monolithic matrix or microcapsule suspension and introducing the drug delivery vehicle suspension into the conjunctival sac of the eye. Similarly, it is also contemplated as being within the scope of the present invention to form an ocular insert from the monolithic matrix and introducing the insert into the conjunctival sac of the eye.

The following examples are illustrative of the erosion and drug release profiles of exemplary drug delivery vehicles produced in accordance with the teachings of the present invention. All of the following examples were conducted utilizing Gantrez AN-169® reportedly having a number-averaged molecular weight of 67,000. Microparticulates ranging in size from 10 to 100 µm were prepared using a solvent evaporation method in which from 2% to 5% by weight of the pharmaceutical compound of choice were dissolved with the polymer in acetonitrile. The solvent was subsequently evaporated to leave behind a homogeneous dry film of drug/polymer matrix which was mechanically ground to the desired particle size. The results from a variety of in vitro and in vivo experiments and acute toxicity tests are summarized as follows:

EXAMPLE 7

In vitro: The dissolution experiment was performed using standard USP methodology with a Hanson dissolution apparatus operated at 37° C. and 50 rpm. The dissolution medium was buffered at pH 7.4 with 0.05M of $KH_2PO_4$, and sink conditions were ensured. The cumulative drug release and the extent of polymer erosion were monitored by assaying the amounts of free drug and free copolymer acid in the aqueous medium using HPLC/UV.

As shown in FIG. 1, the release profile of dipivefrin (DPE) from the monolithic matrix particles was not much affected when the loading was increased from 2% to 5%. The release characteristics are sensitive to the pH of the dissolution medium, however. Accordingly, an organic acid can be incorporated into the matrix to regulate the local pH within the microparticles to slow down the polymer erosion and the drug release rates when the dissolution medium is maintained at pH 7.4, as under physiological conditions. Additionally, as shown in FIG. 1, the polymer erosion rate, and hence the drug release rate, can be further controlled by varying the amount of free acid contained in the polymer. Reducing the free acid content decreases the drug release rate.

Figure 2:
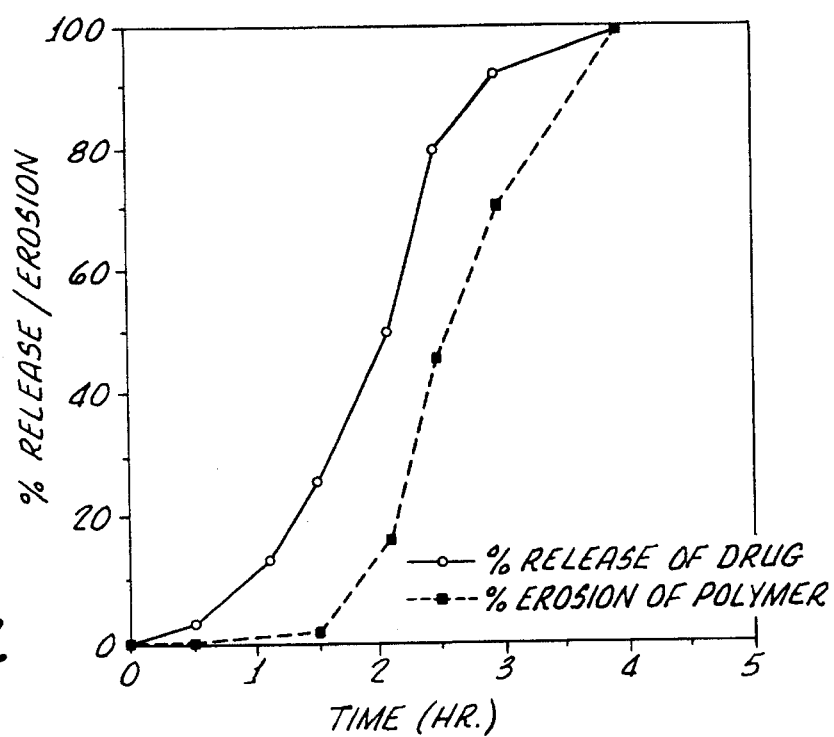
FIG. 2 is a graphical illustration showing the cumulative drug release and polymer erosion of a microparticulate drug delivery vehicle formed in accordance with the teachings of the present invention.

It was also noted that the microparticles tended to agglomerate together to form a translucent gel, which swelled as water penetrated during operation. Thus, the matrix underwent bulk erosion and the drug release rate accelerated after the initial induction period as shown in FIG. 2.

EXAMPLE 8

Figure 3:
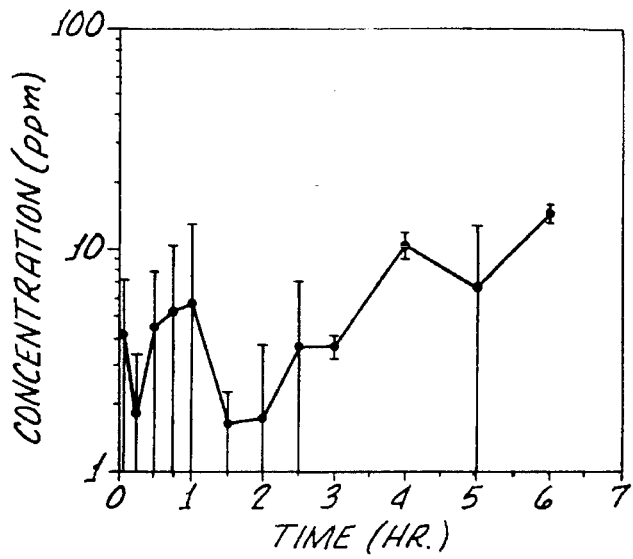
FIG. 3 is a graphical illustration showing the concentration of rhodamine released from an ocular drug delivery vehicle produced in accordance with the teachings of the present invention.
Figure 4:
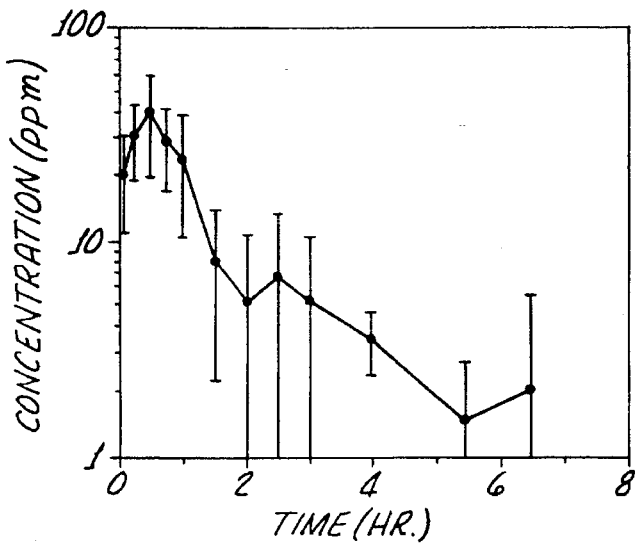
FIG. 4 is a graphical illustration showing the concentration of sodium fluorescein released from a microparticulate drug delivery vehicle formed in accordance with the teachings of the present invention.

In vivo: The release of drug from the Gantrez monolithic matrix in rabbits' eyes was studied by assaying the drug concentration in the tear film over time. To increase the detection limit, either rhodamine 6 G or sodium fluorescein was incorporated in the matrix instead of a drug. A six-hour experiment shows that rhodamine 6 G was released slowly initially and began to increase after four hours while sodium fluorescein (which is extremely hydrophilic) was released primarily in the first hour as shown in FIGS. 3 and 4, respectively.

The hydrophobicity of the dye apparently played a significant role. The in vitro release periods of the above two matrices are four hours (rhodamine) and 0.25 hour (fluorescein), respectively. This demonstrates that the drug release rate is far slower in vivo than in vitro. More particularly, depending upon the animal species utilized, the drug release rate in vivo is slower by a factor of 2–5 than the corresponding drug release rate in vitro. Accordingly, a 24-hour drug release period in vivo is readily achievable by the present invention.

EXAMPLE 9

A retention study of the Gantrez monolithic matrix particles was also conducted in rabbits for six hours. It was found that the microparticles are well retained in the conjunctival sac even after six hours, regardless of the dose volume (20–50 µl) and the particle concentration in the suspension (10–20%). The microparticles swell in the rabbit eye and appeared to stick to the conjunctival sac and to themselves. This is in striking contrast to polystyrene latex beads (14 and 50 µm), which were retained for less than 30 minutes before being expelled from the corner of the eye.

EXAMPLE 10

A pharmacological study was conducted to determine whether the drug delivery system would actually increase the duration of action of a drug preparation. A suspension of microparticulate drug delivery vehicles prepared in accordance with the teachings of the present invention containing 2% by weight dipivefrin was introduced into the eye of each of three owl monkeys. Net amount of drug administered into each eye was 5 µg and the dose volume was 10 µl. A control group was dosed with a 0.05% dipivefrin aqueous solution. Intraocular pressure (IOP) measurements were taken each hour at zero through six hours while the subjects were restrained.

Figure 5:
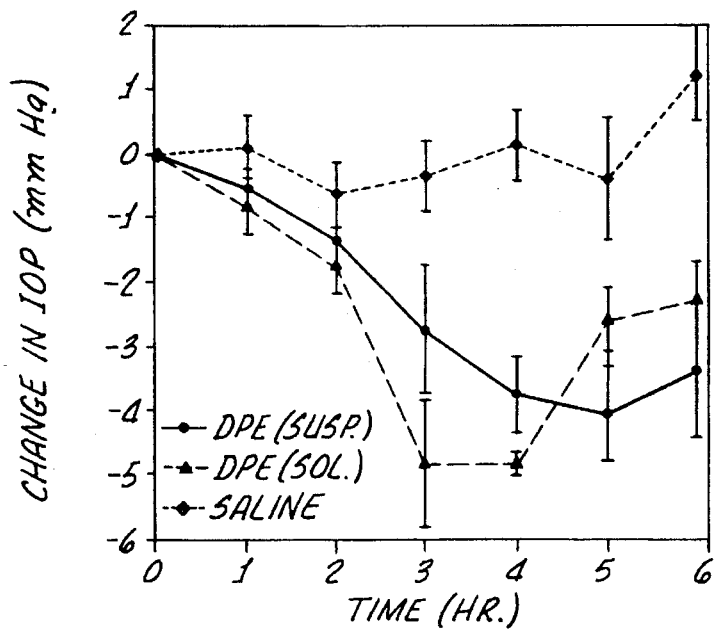
FIG. 5 is a graphical illustration showing the change in intraocular pressure (IOP) as a result of dipivefrin (DPE) administration in accordance with the teachings of the present invention.

As shown in FIG. 5, the IOP lowering effect of the microparticulate suspension extended for a longer duration than did that of the aqueous solution.

EXAMPLE 11

A probe acute toxicity test was conducted for one day on the Gantrez monolithic matrix microparticles loaded with 5% sodium fluorescein. Suspension concentrations of 2.5% and 10% were studied. Both samples were found to be only slightly discomforting to the eye, non-irritating to the conjunctiva, and not toxic or cytotoxic to the cornea.

Hydrolysis rate experiments of alternative molecular weight copolymers were conducted to determine the common functional performance characteristics of several copolymers within the scope of the present invention as follows.

EXAMPLE 12

0.05 g of Gantrez AN119 powder, mw 20,000, (number-averaged as reported by GAF) was dispersed in 100 ml of water, which was controlled at pH 9.5 by titration of 0.1M NaOH using a Radiometer autotitrator at room temperature. The particle size of the copolymer was 23 µm as determined by laser light scattering. Complete hydrolysis of the AN119 copolymer was observed after 10 hours. Similar experiments showed that the complete hydrolysis of AN139 (mw 41,000), AN169 (mw 67,000), and AN179 (mw 80,000) took 6.5 hours, 12 hours, and 9.5 hours, respectively.

Similarly, microspheres and microparticules were formed from alternative copolymers within the scope of the present invention as illustrated in the following non-limiting examples.

EXAMPLE 13

2.0 g of Gantrez AN119 and 0.05 g of dipivefrin hydrochloride were dissolved in 25 ml of acetone to form a solution at room temperature. An oil phase containing 0.3 g of soybean lecithin and 150 ml of light/heavy mineral oil (50/50) was separately prepared. The acetone solution was slowly dropped into the oil phase with stirring. The temperature of the oil phase was maintained at 25° C., and the acetone was evaporated overnight. The resulting microspheres in the oil phase were washed with petroleum ether and were dried. The average size of the microspheres was 43 µm.

EXAMPLE 14

0.1 g of acid orange dye and 4.9 g of AN179 were dissolved in 200 ml of dimethyl formamide to form a solution at room temperature in a round bottom flask. Dimethyl formamide was subsequently removed by rotor-evaporation at 80° C. under high vacuum. The resulting solid film was ground into microparticles with a Tekmar mill and dry ice. The average particle size was 20 µm. The dye loading in the matrix was 2.01% w/w as determined by a UV spectrophotometer.

Hydrolysis rate experiments of exemplary alternative copolymers were conducted as follows.

EXAMPLE 15

0.05 g of poly(ethylene/maleic anhydride) powder (Polysciences) was added into 80 mL of water, and the polymer immediately agglomerated to form a clear gel. The pH of the aqueous system was controlled at 9.5 by titration of 0.1M NaOH using a Radiometer autoitrator at room temperature. Complete hydrolysis of the copolymer was observed after 45 minutes. The gel totally disappeared and the aqueous solution was clear at the end of the hydrolysis experiment.

EXAMPLE 16

0.05 g of poly(butadiene/maleic anhydride) copolymer was added into 80 mL of water from an acetone solution. A yellow opaque gel formed instantly in the water. The sample was then subjected to the routine pH-stat hydrolysis experiment at pH 9.5 as described in the previous example. The copolymer was slow to hydrolyze. About 50% of the poly(butadiene/maleic anhydride) copolymer was hydrolyzed after 24 hours, and complete hydrolysis of the copolymer took 3 days.

Having thus described preferred exemplary embodiments of the present invention, it should be noted by those skilled in the art that the disclosures herein are exemplary only and that alternatives, adaptations and modifications may be made within the scope of the present invention. Thus, by way of example and not limitation, it is contemplated that alternative forms of the polymer delivery vehicle may be utilized. Such forms may include layered inserts with graded concentrations of pharmaceutical compound to produce alternative drug delivery profiles. Additionally, the Gantrez AN-169 copolymer may be substituted by the following copolymers and hompolymers (The ratio of monomers is given in parts per hundred):

75 maleic anhydride/25 methylvinylether
25 maleic anhydride/75 methylvinylether
50 maleic anhydride/50 propylvinylether
50 maleic anhydride/50 n-butylacrylate
50 maleic anhydride/50 vinylacetate
50 maleic anhydride/50 ethylene
50 maleic anhydride/50 styrene
50 maleic anhydride/25 vinylchloride/25 2-ethylhexylacrylate
50 maleic anhydride/50 methylmaleic anhydride
50 maleic anhydride/50 vinylidene chloride
100 butylmaleic anhydride Accordingly, the present invention is not limited to the specific embodiments illustrated herein.

I claim:

1. An erodible, self-lubricating, bio-adhesive drug delivery vehicle consisting essentially of:
   homogeneous poly(methylvinylether/maleic anhydride) copolymer; and
   from approximately 1% to 60% by weight therapeutic or diagnostic pharmaceutical compound incorporated therein, wherein said vehicle erodes by hydrolysis of the maleic anhydride units to provide two carboxylic radicals for each maleic anhydride unit and said copolymer has a ratio of carbon atoms to carboxylic radicals of about 3.5.

2. The drug delivery vehicle of claim 1 wherein said pharmaceutical compound is incorporated within said homogeneous copolymer to form a monolithic matrix.

3. The drug delivery vehicle of claim 2 wherein said monolithic matrix comprises a plurality of microparticulates, said microparticulates being sized from approximately 2 μm to approximately 200 μm.

4. The drug delivery vehicle of claim 3 wherein said plurality of microparticulates are suspended in a liquid carrier.

5. The drug delivery vehicle of claim 2 wherein said monolithic matrix is formed to produce an insert sized from approximately 500 μm to approximately 5000 μm.

6. The drug delivery vehicle of claim 2 wherein said pharmaceutical compound is present at a concentration of approximately 1% to 20% by weight.

7. A dropable or injectable self-lubricating, self-adhesive, bio-adhesive, erodible drug delivery vehicle comprising:
   a microparticulate suspension of a monolithic matrix of claim 2 and a pharmaceutically effective amount of a therapeutic or diagnostic/pharmaceutical compound, each of said microparticulates being sized from approximately 2 μm to approximately 200 μm, wherein said vehicle erodes by hydrolysis of the maleic anhydride units to provide two carboxylic radicals for each maleic anhydride unit and said copolymer has a ratio of carbon atoms to carboxylic radicals of about 3.5.

8. An erodible, self-lubricating, self-adhesive, bio-adhesive drug delivery vehicle comprising an insert formed of a monolithic matrix of the vehicle of claim 2 and a pharmaceutically effective amount of a therapeutic or diagnostic pharmaceutical compound, said insert being sized from approximately 500 μm to approximately 5000 μm, wherein said vehicle erodes by hydrolysis of the maleic anhydride units to provide two carboxylic radicals for each maleic anhydride unit and said copolymer has a ratio of carbon atoms to carboxylic radicals of about 3.5.

9. The drug delivery vehicle of claim 1 wherein said pharmaceutical compound is encapsulated by said homogeneous copolymer to form a plurality of microcapsules.

10. The drug delivery vehicle of claim 9 wherein each of said microcapsules is sized from approximately 2 μm to approximately 200 μm.

11. The drug delivery vehicle of claim 9 wherein said microcapsules are suspended in a liquid carrier.

12. The drug delivery vehicle of claim 9 wherein said pharmaceutical compound is present at a concentration of approximately 2% to 60% by weight.

13. The drug delivery vehicle of claim 1 wherein said pharmaceutical compound is selected from the group consisting of antibacterials, antiinflammatories, miotics, mydriatics, antiglaucoma compounds, antivirals, carbonic anhydrase inhibitors, anti-fungal agents, anesthetic agents, diagnostic agents and immunosuppressive agents.

14. The drug delivery vehicle of claim 1 wherein said pharmaceutical compound is selected from the group consisting of dipivalyl epinephrine hydrochloride (DPE), levobunolol hydrochloride, flurbiprofen, 5-bromo-6-(imidazolin-2-ylamino)quinoxaline, pilocarpine, sodium fluorescein, timolol, betaxolol, ofloxacin and ibuprofen.

15. A dropable or injectable self-lubricating, self-adhesive, bio-adhesive, erodible drug delivery vehicle comprising a plurality of microcapsules, each of said microcapsules formed of approximately 5% to 60% by weight therapeutic or diagnostic pharmaceutical compound encapsulated by the vehicle of claim 1, wherein said vehicle erodes by hydrolysis of the maleic anhydride units to provide two carboxylic radicals for each maleic anhydride unit and said copolymer has a ratio of carbon atoms to carboxylic radicals of about 3.5.

16. A method for delivering a pharmaceutical compound to the eye, said method comprising the steps of:
   preparing a dropable or injectable suspension of self-lubricating, erodible, self-adhesive, bio-adhesive microcapsules, each of said microcapsules being formed of from approximately 2% to 60% by weight of said pharmaceutical compound encapsulated in the vehicle of claim 1; and
   introducing said suspension into the conjunctival sac of the eye, wherein said microcapsules erode by hydrolysis of the maleic anhydride units to provide two carboxylic radicals for each maleic anhydride unit and said copolymer has a ratio of carbon atoms to carboxylic radicals of about 3.5.

17. The drug delivery vehicle of claim 1 wherein said pharmaceutical compound is selected from the group consisting of antihistaminics, anticholinergics and antiparasitic compounds.

18. A method for delivering a pharmaceutical compound to the eye, said method comprising the steps of:
   preparing an erodible, self-lubricating, self-adhesive, bioadhesive monolithic matrix consisting essentially of homogeneous poly(methylvinylether/maleic anhydride) copolymer and a pharmaceutically an effective concentration of at least one pharmaceutical compound; and introducing said monolithic matrix into the conjunctival sac of the eye, wherein said copolymer erodes by hydrolysis of the maleic anhydride units to provide two carboxylic radicals for each maleic anhydride unit and said copolymer has a ratio of carbon atoms to carboxylic radicals of about 3.5.

19. The method of claim 18 further comprising the additional step of:

forming a microparticulate suspension of said monolithic matrix prior to introducing the matrix into said conjunctival sac.

20. The method of claim 18 further comprising the additional step of:

forming an ocular insert from said monolithic matrix prior to introducing the matrix into said conjunctival sac.

21. An erodible, self-lubricating, bio-adhesive drug delivery vehicle consisting essentially of:

a lower alkyl maleic anhydride or maleic anhydride homogeneous copolymer of the formula

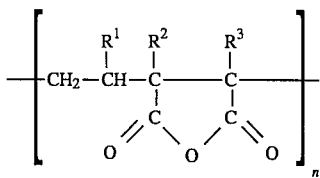

wherein $R^1$ is $C_{1-4}$ alkyl, alkylether, alkylester, or halogen;

$R^2$ and $R^3$ are each selected from the group consisting hydrogen and $C_{1-4}$; and from approximately 1% to 60% by weight therapeutic or diagnostic pharmaceutical compound incorporated therein, wherein said vehicle erodes by hydrolysis of the maleic anhydride or lower alkyl maleic anhydride units to provide two carboxylic radicals for each maleic anhydride unit and said copolymer has a ratio of carbon atoms to carboxylic radicals ranging from about 3 to 7.

22. An erodible, self-lubricating, bio-adhesive drug delivery vehicle consisting essentially of:

a maleic anhydride or a lower alkyl maleic anhydride homogeneous homopolymer or copolymer; and from approximately 1% to 60% by weight therapeutic or diagnostic pharmaceutical compound incorporated therein, wherein said vehicle erodes by hydrolysis of the maleic anhydride or lower alkyl maleic anhydride units to provide two carboxylic radicals for each anhydride unit and said polymer has a ratio of carbon atoms to carboxylic radicals ranging from 2 to 7.

23. The vehicle of claim 22 wherein said ratio of carbon atoms to carboxylic radicals ranges from 3 to 7.

24. The vehicle of claim 22 comprising a maleic anhydride copolymer.

25. The vehicle of claim 23 comprising a hydrocarbon comonomer or a hydrocarbon comonomer substituted with non-hydrophilic substituents selected from the group consisting of —X, —O—R,

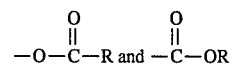

wherein X is a halogen radical and R is an alkyl radical having from 1 to 12 carbon atoms.

26. The vehicle of claim 25 wherein said comonomer is selected from the group consisting of $C_1$ to $C_4$ lower alkyl vinylethers wherein the alkyl chain comprises from 1 to 4 carbon atoms, butadiene, styrene, isoprene, ethylene, propylene, vinylchloride and alkylesters, said alkylesters selected from the group consisting of acrylic acid having from 1 to 8 carbon atoms in the alkyl chain and methacrylic acid having from 1 to 8 carbon atoms in the alkyl chain.

27. A method for delivering a pharmaceutical compound to the eye, said method comprising the steps of:

preparing an erodible, self-lubricating, self-adhesive, bio-adhesive monolithic matrix consisting essentially of a maleic anhydride or a lower alkyl maleic anhydride homogeneous homopolyer or copolymer and a pharmaceutically effective concentration of at least one pharmaceutical compound; and introducing said monolithic matrix into the conjunctival sac of the eye, wherein said matrix erodes by hydrolysis of the maleic anhydride or lower alkyl maleic anhydride units to provide two carboxylic radicals for each anhydride unit and said polymer has a ratio of carbon atoms to carboxylic radicals from 2 to 7.

28. The vehicle of claim 27 wherein said ratio of carbon atoms to carboxylic radicals ranges from 3 to 7.

29. The vehicle of claim 27 comprising a homogeneous maleic anhydride copolymer.

30. The vehicle of claim 28 comprising a hydrocarbon comonomer or a hydrocarbon comonomer substituted with non-hydrophilic substituents selected from the group consisting of —X, —O—R,

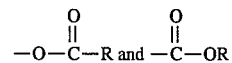

wherein X is a halogen radical and R is an alkyl radical having from 1 to 12 carbon atoms.

31. The vehicle of claim 30 wherein said comonomer is selected from the group consisting of $C_1$ to $C_4$ lower alkyl vinylethers wherein the alkyl chain comprises from 1 to 4 carbon atoms, butadiene, styrene, isoprene, ethylene, propylene, vinylchloride and alkylesters, said alkylesters selected from the group consisting of acrylic acid having from 1 to 8 carbon atoms in the alkyl chain and methacrylic acid having from 1 to 8 carbon atoms in the alkyl chain.

32. A method for delivery a pharmaceutical compound to the eye, said method comprising the steps of:

preparing a dropable or injectable suspension of self-lubricating, erodible, self-adhesive, bio-adhesive microcapsules, each of said microcapsules being formed of from approximately 2% to 60% by weight of said pharmaceutical compound encapsulated in the vehicle of claim 22 and introducing said suspension into the conjunctival sac of the eye, wherein said microcapsules erode by hydrolysis of the maleic anhydride or lower alkyl maleic anhydride units of the vehicle to provide two carboxylic radicals for each maleic anhydride unit and said polymer has a ratio of carbon atoms to carboxylic radicals from 2 to 7.

33. The method of claim 32 wherein said ratio of carbon atoms to carboxylic radicals ranges from 3 to 7.

34. The method of claim 32 comprising a maleic anhydride copolymer.

35. The method of claim 33 comprising a hydrocarbon comonomer or a hydrocarbon comonomer substituted with non-hydrophilic substituents selected from the group consisting of —X, —O—R,

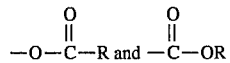

wherein X is a halogen radical and R is an alkyl radical having from 1 to 12 carbon atoms.

36. The method of claim 35 wherein said comonomer is selected from the group consisting of $C_1$ to $C_4$ lower alkyl vinylethers wherein the alkyl chain comprises from 1 to 4 carbon atoms, butadiene, styrene, isoprene, ethylene, propylene, vinylchloride and alkylesters, said alkylesters selected from the group consisting of acrylic acid having from 1 to 8 carbon atoms in the alkyl chain and methacrylic acid having from 1 to 8 carbon atoms in the alkyl chain.

* * * * *